A61N 2005/1022 (2013.01); A61N 2005/1088 (2013.01); A61N 2005/1089 (2013.01); H01S 3/0057 (2013.01); H01S 3/11 (2013.01); H01S 3/1625 (2013.01)

(12) United States Patent
Mao et al.

(10) Patent No.: US 10,433,412 B2
(45) Date of Patent: Oct. 1, 2019

(54) SHOCK INJECTOR FOR LOW-LASER ENERGY ELECTRON INJECTION IN A LASER PLASMA ACCELERATOR

(71) Applicant: The Regents of the University of California, Oakland, CA (US)

(72) Inventors: Hann-Shin Mao, Richmond, CA (US); Wim Leemans, Kensington, CA (US); Stepan Bulanov, Concord, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/894,422

(22) Filed: Feb. 12, 2018

(65) Prior Publication Data
US 2018/0168024 A1 Jun. 14, 2018

Related U.S. Application Data

(63) Continuation of application No. PCT/US2016/046746, filed on Aug. 12, 2016.
(Continued)

(51) Int. Cl.
| | |
|---|---|
| *H05H 1/54* | (2006.01) |
| *H05H 15/00* | (2006.01) |
| *A61N 5/10* | (2006.01) |
| *G21K 5/02* | (2006.01) |
| *H01S 3/00* | (2006.01) |
| *H01S 3/11* | (2006.01) |
| *H01S 3/16* | (2006.01) |

(52) U.S. Cl.
CPC .............. *H05H 1/54* (2013.01); *A61N 5/1001* (2013.01); *A61N 5/1007* (2013.01); *G21K 5/02* (2013.01); *H05H 15/00* (2013.01); *A61N*

(58) Field of Classification Search
CPC ............ H05H 1/54; H05H 15/00; G21K 5/02
See application file for complete search history.

(56) References Cited

U.S. PATENT DOCUMENTS

| | | | |
|---|---|---|---|
| 3,904,985 | A | 9/1975 | Robinson et al. |
| 6,133,577 | A | 10/2000 | Gutowski et al. |
| (Continued) | | | |

OTHER PUBLICATIONS

International Search Report and Written Opinion for International Application No. PCT/US2016/046746 dated Oct. 28, 2016.
(Continued)

*Primary Examiner* — Eliza W Osenbaugh-Stewart

(57) ABSTRACT

This disclosure provides systems, methods, and apparatus related to laser plasma accelerators. In one aspect a block of material defines a gas inlet, a chamber in fluid communication with the gas inlet, a throat in fluid communication with the chamber, a channel in fluid communication with the throat, and a gas outlet in fluid communication with the channel. The throat is configured to generate a supersonic flow of a gas when the gas flows through the throat. The channel includes a ramp that is positioned proximate the gas outlet, with the ramp being inclined at an angle with respect to a direction of a flow of the gas proximate a surface of the channel prior to the ramp at the gas outlet.

19 Claims, 15 Drawing Sheets

Related U.S. Application Data

(60) Provisional application No. 62/207,193, filed on Aug. 19, 2015, provisional application No. 62/333,433, filed on May 9, 2016.

(56) References Cited

U.S. PATENT DOCUMENTS

| | | |
|---|---|---|
| 8,672,644 B2 | 3/2014 | Kidd et al. |
| 8,705,692 B2 | 4/2014 | Umstadter et al. |
| 8,878,464 B2 | 11/2014 | Clayton et al. |
| 9,022,914 B2 | 5/2015 | Clayton et al. |
| 2009/0218521 A1 | 9/2009 | Sogard et al. |
| 2012/0080618 A1 | 4/2012 | Clayton et al. |
| 2014/0166051 A1 | 6/2014 | Umstadter et al. |
| 2014/0254766 A1* | 9/2014 | Sylla .............. H05G 2/006 378/119 |
| 2016/0014874 A1* | 1/2016 | Kaganovich ...... H05G 2/008 378/119 |
| 2016/0244177 A1* | 8/2016 | Adamson .......... B64D 33/02 |

OTHER PUBLICATIONS

Suk, H., et al. "Plasma Electron Trapping and Acceleration in a Plasma Wake Field Using a Density Transition." Physical Review Letters 86 (2001): 1011-1014.

W. P. Leemans et al. "Plasma Guiding and Wakefield Generation for Second-Generation Experiments." IEEE Transactions on Plasma Science, vol. 24, No. 2, Apr. 1996, pp. 331-342.

\* cited by examiner

US 10,433,412 B2

SHOCK INJECTOR FOR LOW-LASER ENERGY ELECTRON INJECTION IN A LASER PLASMA ACCELERATOR

RELATED APPLICATIONS

This application claims priority to International Application No. PCT/US2016/046746, filed Aug. 12, 2016, which claims priority to U.S. Provisional Patent Application No. 62/207,193, filed Aug. 19, 2015 and to U.S. Provisional Patent Application No. 62/333,433, filed May 9, 2016, all of which are herein incorporated by reference.

STATEMENT OF GOVERNMENT SUPPORT

This invention was made with government support under Contract No. DE-AC02-05CH11231 awarded by the U.S. Department of Energy. The government has certain rights in this invention.

TECHNICAL FIELD

This disclosure relates generally to laser plasma accelerators and laser plasma acceleration.

BACKGROUND

Methods and devices for generating a gas having two regions of different gas density, without mixing of the regions in space, are used in laser plasma accelerators (LPAs). The gas is used as a target in a LPA. A density transition in a gas that occurs over a short distance, which may be referred to as a sharp density transition, has been shown to aid electron injection in LPAs. The sharp density transition makes electron injection possible at millijoule (mJ) level laser energies with atmospheric to sub-atmospheric gas densities.

SUMMARY

One innovative aspect of the subject matter described in this disclosure can be implemented in a device including a block of material. The block of material defines a gas inlet, a chamber in fluid communication with the gas inlet, a throat in fluid communication with the chamber, a channel in fluid communication with the throat, and a gas outlet in fluid communication with the channel. The throat is configured to generate a supersonic flow of a gas when the gas flows through the throat. The channel includes a ramp that is positioned proximate the gas outlet, with the ramp being inclined at an angle with respect to a direction of a flow of the gas proximate a surface of the channel prior to the ramp at the gas outlet. The chamber, the throat, and the channel are defined by a first, a second, a third, and a fourth surface. The first surface and the second surface are substantially flat surfaces and are substantially parallel to one another. A distance between a third surface and a fourth surface defining the channel increases from a region of the channel proximate the throat to a region proximate the gas outlet.

Another innovative aspect of the subject matter described in this disclosure can be implemented in an apparatus including a block of material, a laser system, and an optical fiber. The block of material defines a gas inlet, a chamber in fluid communication with the gas inlet, a throat in fluid communication with the chamber, a channel in fluid communication with the throat, and a gas outlet in fluid communication with the channel. The throat is configured to generate a supersonic flow of a gas when the gas flows through the throat. The channel includes a ramp that is positioned proximate the gas outlet, with the ramp being inclined at an angle with respect to a direction of a flow of the gas proximate a surface of the channel prior to the ramp at the gas outlet. The chamber, the throat, and the channel are defined by a first, a second, a third, and a fourth surface. The first surface and the second surface are substantially flat surfaces and are substantially parallel to one another. A distance between a third surface and a fourth surface defining the channel increases from a region of the channel proximate the throat to a region proximate the gas outlet. The laser system is configured to generate a laser pulse. The optical fiber is coupled to the laser system and configured to guide the laser pulse. An end of the optical fiber is positioned to direct the laser pulse through the gas when the gas is flowing from the gas outlet.

Another innovative aspect of the subject matter described in this disclosure can be implemented in a method including generating a flow of a gas including a first region having a first gas density and a second region having a second gas density. A transition region between the first region and the second region is an oblique shock wave having a width of less than about 5 microns. The first gas density is about 1.5 to 2.5 times the second gas density. A laser pulse is directed to impinge on the gas flow. The laser pulse travels through the first region and then the second region. The laser pulse generates a pulse of accelerated electrons.

Details of one or more embodiments of the subject matter described in this specification are set forth in the accompanying drawings and the description below. Other features, aspects, and advantages will become apparent from the description, the drawings, and the claims. Note that the relative dimensions of the following figures may not be drawn to scale.

DETAILED DESCRIPTION

Figure 1A:
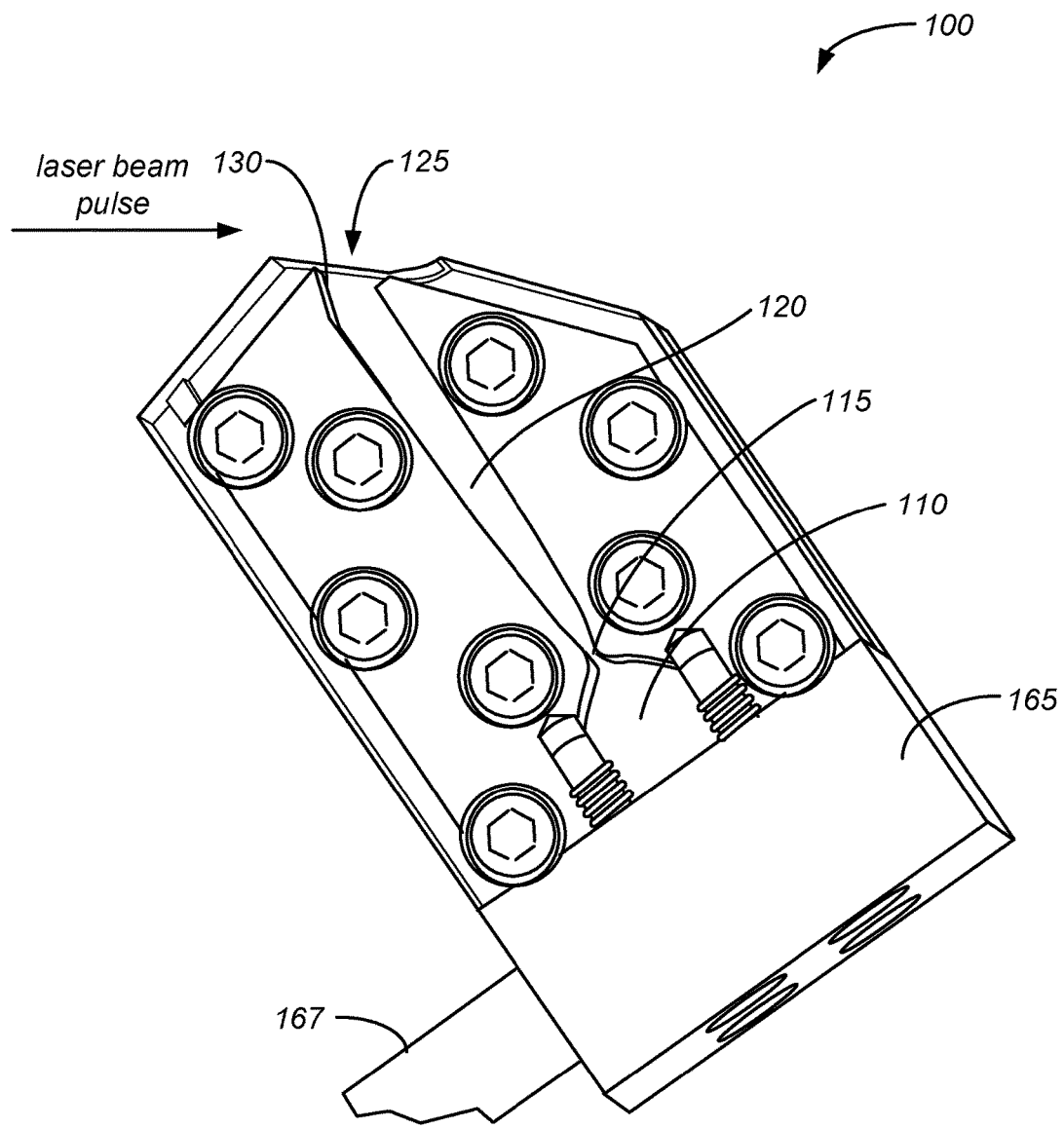
FIGS. 1A and 1B show examples of illustrations of a shock injector.

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise.

The terms "about" or "approximate" and the like are synonymous and are used to indicate that the value modified by the term has an understood range associated with it, where the range can be ±10%, ±5%, or ±1%. The term "substantially" is used to indicate that a value is close to a targeted value, where close can mean, for example, the value is within 90% of the targeted value, within 95% of the targeted value, or within 99% of the targeted value.

Laser plasma acceleration, or LPA, is a technique to produce relativistic electrons using a high-intensity laser and a plasma. Due to the electromagnetic properties of plasma, a high intensity, coherent, electromagnetic femtosecond pulse (also referred to as a laser pulse herein) will drive a trailing density perturbation, known as a wake, in the plasma electron density as it travels through the plasma. The strength of this wake is determined by the intensity of the laser pulse, which is controlled by the amplitude, the pulse duration, and the focal volume of the laser pulse, and the background plasma density. The wake structure of the plasma electrons exists over a uniform distribution of positively charged heavy ions which are immobile in the femtosecond timescale of the laser pulse. This disparity in density between the electron wake and the ion background creates a strong potential gradient capable of accelerating electrons to relativistic energies. If the wake amplitude is large enough, electron injection can occur in which electrons that are phased correctly are deposited into the acceleration wake. The electrons then accelerate behind the laser pulse until both the laser pulse and the now relativistic electron beam exit the plasma.

The generation of the plasma can be performed in several ways. One common way is to allow the laser pulse to ionize a section of neutral gas. If the laser pulse has sufficient intensity, the laser will effectively strip electrons off the neutral gas transforming it into a plasma. Provided that the laser energy is high enough, the ionization is confined to the front of the laser pulse, which allows the remaining laser pulse to drive the wake used for electron acceleration. Because the laser pulse duration is on the femtosecond timescale and travels at the speed of light, the neutral gas density profile before ionization can be taken as the plasma density profile. This allows for neutral gas density tailoring, which can be performed using a supersonic jet of a neutral gas species. Supersonic flow is where the gas is flowing faster than the speed of sound, which is the maximum velocity at which density disturbances can propagate through a flow. As such, supersonic flow can sustain features such as shock waves and rarefaction fans. These can be used to create special features in the plasma density profile to aid in electron injection.

One such feature that greatly aids electron injection is a sharp density drop in the gas/plasma. With a sharp density drop, the laser initially drives a wake in a high density region of the plasma. As the laser propagates into the low density region of the plasma, the plasma wavelength instantly changes and the wake elongates, which places electrons in the high density region adjacent to the transition into the correct phase for acceleration. The density transition must occur on the length scale of the plasma wavelength, which for a $10^{19}$ electrons/cm$^3$ plasma is on the order of 5 microns. If the transition occurs in a length scale longer than the plasma wavelength, the electrons will not be placed into a proper phase for acceleration. The transition created by a sustained shock wave is on the order of the gas mean free path. This is below 5 microns for the corresponding neutral gas densities for flow velocities larger than Mach 2. Therefore, a shockwave created density transition is appropriate for this method of electron injection.

Some target generation devices (also referred to as target devices herein) for LPAs that generate a density transition in a gas include an obstruction in the path of a pulsed free gas jet that is expelled into a vacuum. This can create a localized density bump in the gas. Other target devices include a plasma structure (e.g., a capillary) into which a supersonic gas jet is pulsed. These target devices can be used to achieve electron injection in LPAs. Such target devices may not, however, generate a density transition in a gas that occurs over a short enough distance for stable low laser energy electron injection.

Some optical fibers have the potential to transport up to about 3 millijoules (mJ), up to about 10 mJ, or up to about 100 mJ of laser energy without sustaining damage. LPAs using current target devices, including free-gas jets and capillaries, may not be capable of generating an electron beam using a fiber optic-delivered laser pulse due to the low laser energy of such a laser pulse.

Figure 11:
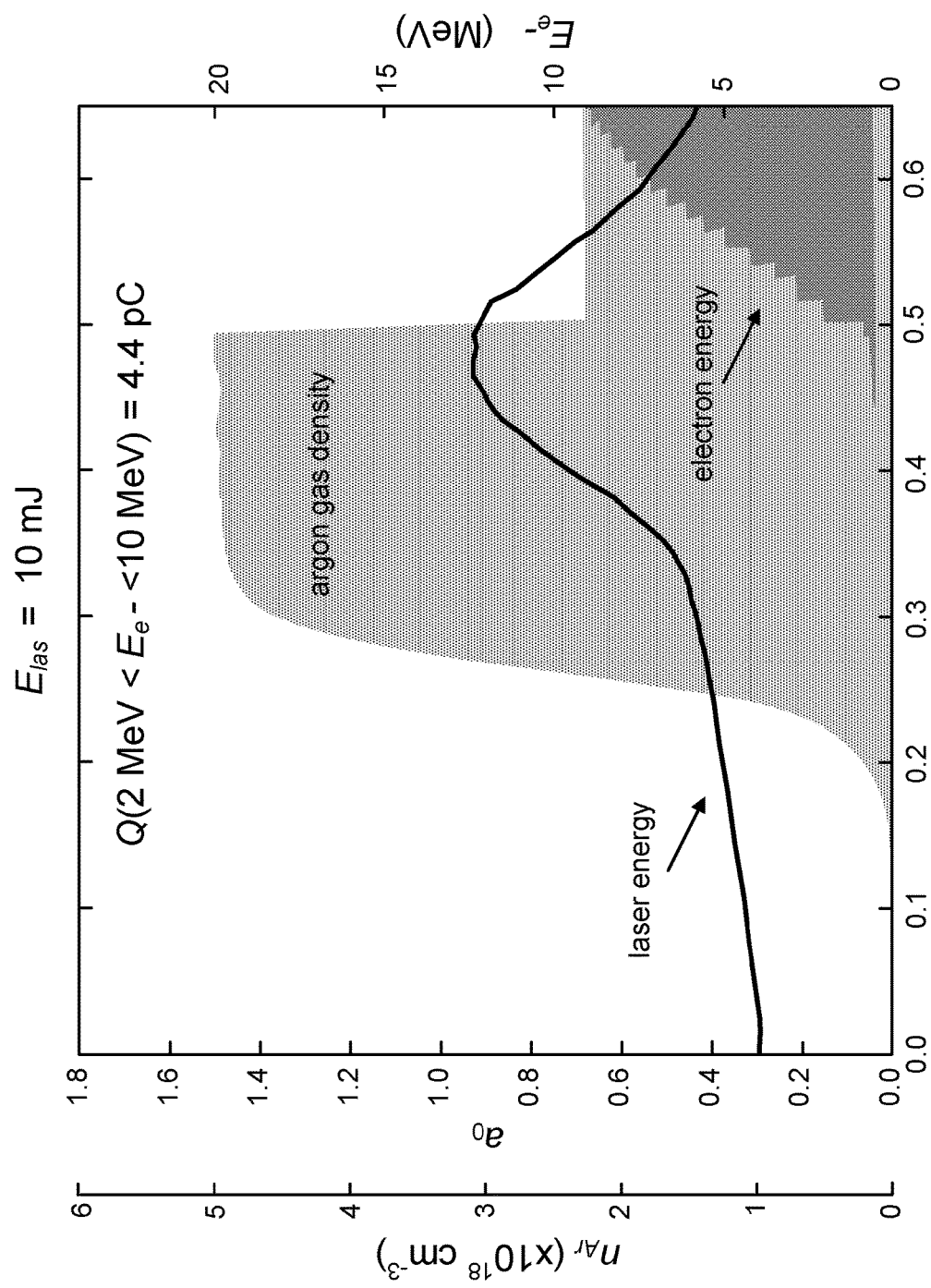
FIG. 11 shows an example of the results of a laser plasma particle in a cell simulation.

Simulations (the results of one simulation are shown in FIG. 11) have shown that electron injection can occur in laser plasma acceleration with about 10 mJ of laser energy if two distinct regions of a gas having different gas densities can be generated. For example, the first gas region may have an electron density of about $4 \times 10^{19}$ electrons/cm$^3$ and a width of about 200 microns. The second gas region may have an electron density of about $2 \times 10^{19}$ electrons/cm$^3$ and a width of about 150 microns. Further, for electron injection, a sharp density transition between the two gas regions needs to occur within the plasma wavelength. The plasma wavelength may be about 2.5 microns to 7.5 microns, or about 5 microns.

A shock injector is a target generation device that can generate a sharp density transition between two gas regions. In some embodiments, a shock injector uses a ramp appended to a supersonic nozzle to create an oblique shock wave (also referred to as an oblique shock). A nozzle is a device designed to control the direction or characteristics of a fluid flow (e.g., to increase velocity) as it exits (or enters) an enclosed chamber or pipe. An oblique shock wave is a shock wave inclined at an oblique angle with respect to the direction of flow in a supersonic flow field. For example, an oblique shock wave can be formed by a sharp-pointed object moving through the air at a speed greater than the speed of sound. An oblique shock wave consists of a thin region across which nearly discontinuous changes in the thermodynamic properties of the gas occur. The supersonic nozzle and the angle of a ramp of the shock injector control the density drop across the shock.

In some embodiments, the supersonic nozzle is designed to produce shock-free flow at a specific Mach number (e.g., about Mach 3). The Mach number is a dimensionless quantity that is the ratio of a flow velocity past a boundary to the local speed of sound. The local speed of sound depends on the characteristics of the surrounding medium, in particular the temperature and pressure. For example, the speed of sound in dry air at 20° C. is 343.2 m/s.

Figure 1B:
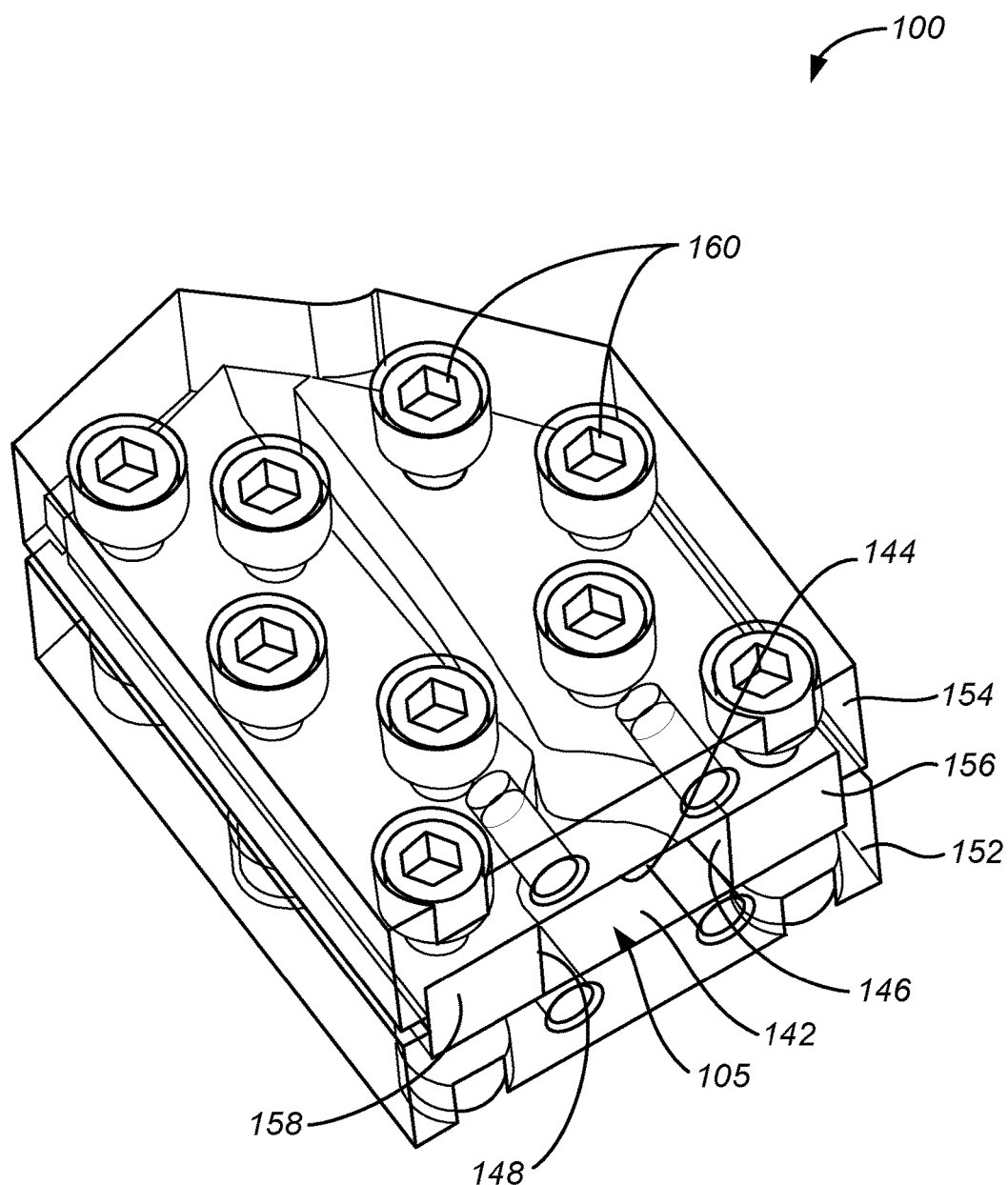

FIGS. 1A and 1B shows examples of illustrations of a shock injector. The shock injector 100 comprises a block of material or blocks of material that define a gas inlet 105, a chamber 110, a throat 115, a channel 120, and a gas outlet 125. The gas inlet 105 is in fluid communication with the chamber 110. The chamber 110 is in fluid communication with the throat 115. The throat 115 is in fluid communication with the channel 120. The channel 120 is in fluid communication with the gas outlet 125. A gas input at the gas inlet 105 of the shock injector 100 will flow through the chamber 110, the throat 115, the channel 120, and exit the shock injector 100 through the gas outlet 125.

In some embodiments, the chamber 110, the throat 115, and the channel 120 are defined by a first surface 142, a second surface 144, a third surface 146, and a fourth surface 148. In some embodiments, the first surface 142 and the second surface 144 are substantially flat and substantially parallel to one another. In some embodiments, a distance between the first surface 142 and the second surface 144 is about 300 microns to 1 millimeter (mm), or about 500 microns. A distance between the third surface 146 and the fourth surface 148 define dimensions of the gas inlet 105, the chamber 110, the throat 115, the channel 120, and the gas outlet 125 so that these features are distinguished from one another in the shock injector 100.

As shown in FIG. 1B, in some embodiments, the shock injector 100 includes four separate blocks of material 152, 154, 156, and 158. The block of material 152 defines the first surface 142. The block of material 154 defines the second surface 144. The block of material 156 defines the third surface 146. The block of material 158 defines the fourth surface 148. In some embodiments, the four separate blocks of material 152, 154, 156, and 158 may be joined to each other with a plurality of fasteners 160. For example, the plurality of fasteners may include screws or nuts and bolts. In some embodiments, the blocks of material 152, 154, 156, and 158 comprise a polymer, such as an acrylic glass. An acrylic glass may also be referred to as poly(methyl methacrylate) (PMMA) or acrylic.

In some embodiments, the shock injector 100 includes a gas routing device 165. The gas routing device 165 may include an internal chamber (not shown) and a hollow tube 167. In some embodiments, the gas routing device 165 serves to direct a gas flow to the gas inlet 105. The gas routing device 165 may make it easier to direct a gas flow through the gas inlet by allowing a tube to carry the gas flow to the hollow tube 167 of the gas routing device 165.

In some embodiments, a distance between the third surface 146 and the fourth surface 148 defining the gas inlet 105 may be about 500 microns to 10 mm. In some embodiments, a distance between the third surface 146 and the fourth surface 148 defining the gas outlet 125 may be about 250 microns to 1 mm.

In some embodiments, a distance between the third surface 146 and the fourth surface 148 defining the throat 115 may be about 20 microns to 100 microns. In some embodiments, the throat 115 is configured to generate a supersonic flow of a gas when gas flows through the throat 115. The pressure of the gas and the dimension of the throat may be specified so that the gas has a supersonic velocity after passing through the throat 115. In some embodiments, the velocity of the gas after passing through the throat 115 is Mach 1.

In some embodiments, a distance between the third surface 146 and the fourth surface 148 defining the channel 120 increases from the throat 115 to the gas outlet 125. The channel 120 includes a ramp 130 that is positioned proximate or at the gas outlet 125. In some embodiments, dimensions of the channel 120 are specified so that no shock waves are generated in the gas flow until the gas flows past the ramp 130. In some embodiments, dimensions of the channel 120 are specified so that flow of a gas through the channel 120 is parallel after the gas passes through the throat 115. In some embodiments, dimensions of the channel 120 are specified so that a gas has a specified velocity or a specified Mach number (e.g., about Mach 2 to Mach 6, or about Mach 3) at the gas outlet 125.

The ramp 130 is inclined at an angle with respect to a direction of a flow of the gas proximate a surface of the channel 120 prior to the ramp at the gas outlet 125. The direction of the flow of the gas proximate a surface 148 of the channel 120 may generally be considered to be parallel to the surface 148 of the channel 120 before the ramp 130. In some embodiments, flow of the gas within about 5 microns of the surface 148 of the channel 120 is parallel to the surface 148. In some embodiments, the ramp 130 is angled at about 15 degrees to 45 degrees, or about 30 degrees, with respect to the direction of the flow of the gas proximate the surface 148 of a channel 120 prior to the ramp 130, with the ramp 130 being angled towards the gas. In some embodiments, the ramp 130 is configured to generate an oblique shock wave in the gas when a gas is flowing through the shock injector 100. The velocity of the gas (i.e., Mach number) and the angle at which the ramp 130 is inclined will determine, in part, the angle of the oblique shock wave with respect to the direction of a flow of the gas at the gas outlet 125.

The oblique shock wave separates two regions of the gas flow, a high gas density region and a low gas density region. In some embodiments, the high gas density region has a density about 1.5 to 2.5 times, or about 2 times, higher than the density of the gas in the low gas density region. The gas density in each region depends in part on the number of ionization levels of the gas being used. For example, when in operation with a laser pulse impinging on the gas flow, the plasma density of the plasma generated in the high gas density region may be about $2\times10^{19}$ electrons per centimeter cubed (electrons/cm$^3$) to $6\times10^{19}$ electrons/cm$^3$, or about $4\times10^{19}$ electrons/cm$^3$. The plasma density of the plasma generated in the low gas density region may be about $1\times10^{19}$ electrons/cm$^3$ to $3\times10^{19}$ electrons/cm$^3$, or about $2\times10^{19}$ electrons/cm$^3$. When the gas being used is argon, which has eight ionization levels (i.e., eight electrons in the outer shell that can be removed from the atom), the gas density is the plasma density divided by eight. For example, the gas density in the high gas density region may be about $5\times10^{18}$ atoms per centimeter cubed (atoms/cm$^3$) (corresponding to a plasma density of $4\times10^{19}$ electrons/cm$^3$). The gas density in the low gas density region may be about $2.5\times10^{18}$ atoms/cm$^3$ (corresponding to a plasma density of $2\times10^{19}$ electrons/cm$^3$). When the gas being used is helium, which has two ionization levels (i.e., two electrons in the outer shell that can be removed from the atom), the gas density is the plasma density divided by 2. For example, the gas density in the high gas density region may be about $2 \times 10^{19}$ atoms/cm$^3$ (corresponding to a plasma density of $4 \times 10^{19}$ electrons/cm$^3$). The gas density in the low gas density region may be about $1 \times 10^{19}$ atoms/cm$^3$ (corresponding to a plasma density of $2 \times 10^{19}$ electrons/cm$^3$).

In some embodiments, a width of a transition (i.e., the oblique shock wave) between the high gas density region and the low gas density region is less than about 5 microns. The velocity of the gas (i.e., Mach number) and the angle at which the ramp is inclined will also determine, in part, the density difference between the high gas density region and the low gas density region.

Figure 2:
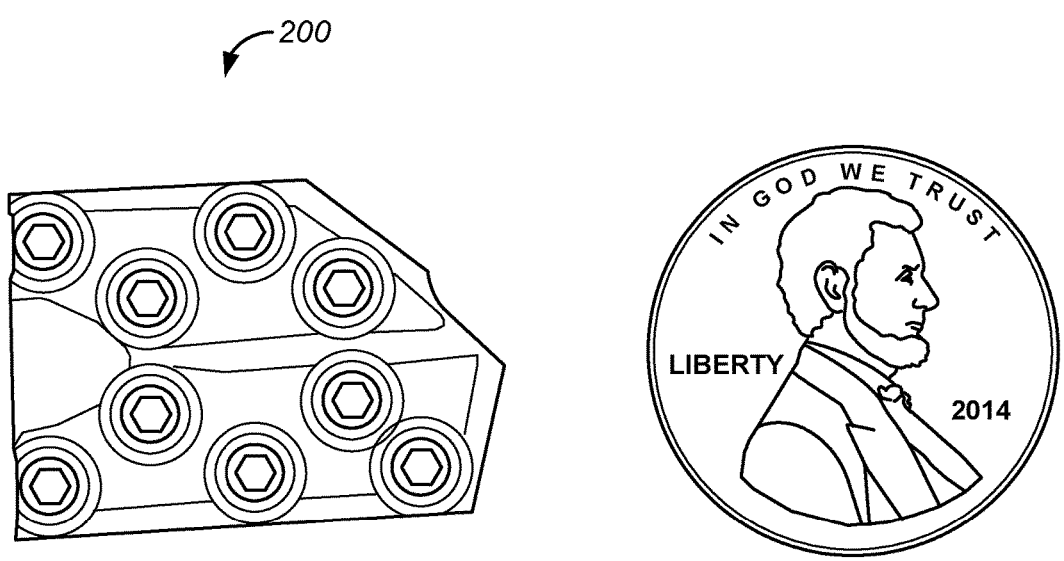
FIG. 2 shows an example of an illustration of a shock injector.

FIG. 2 shows an example of an illustration of a shock injector. The shock injector 200 shown in FIG. 2 is a shock injector that was fabricated with the drawings of the shock injector 100 shown in FIGS. 1A and 1B. A U.S. penny is also shown in FIG. 2 for reference of the size of the shock injector 200.

Figure 3A:
FIGS. 3A and 3B show examples of illustrations of the two density regions in a gas flow from a shock injector.
Figure 3B:
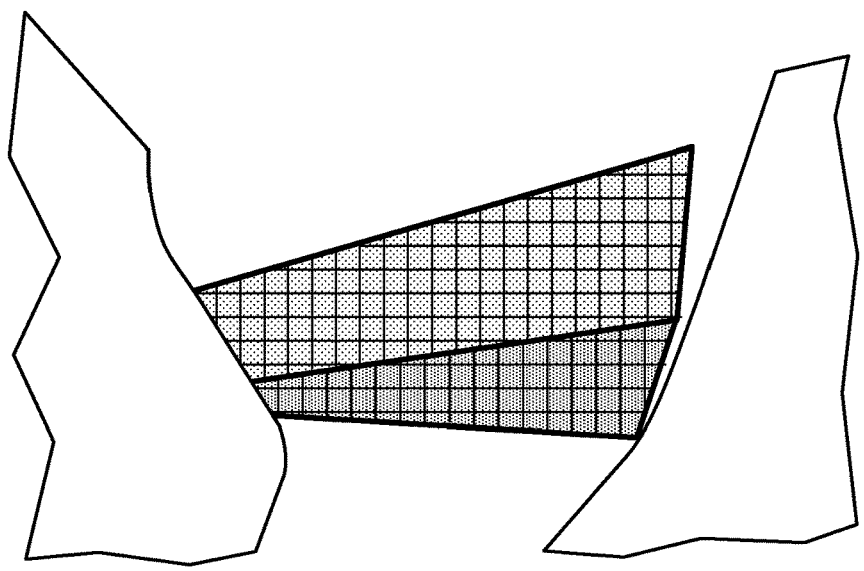

FIGS. 3A and 3B show examples of illustrations of the two density regions in a gas flow from a shock injector. The gas flows shown in FIGS. 3A and 3B were generated using the shock injector 200 shown in FIG. 2. Schlieren imaging was used to show the differences in the gas density in the gas flow that was produced by the shock injector. FIG. 3B (i.e., the inset figure) highlights the density differences in the gas. The lower portion of the gas flow (i.e., the bright region) shown in FIGS. 3A and 3B has a higher density than the upper portion of the gas flow. The transition between the lower portion of the gas flow and the upper portion of the gas flow is an oblique shock wave.

Figure 4:
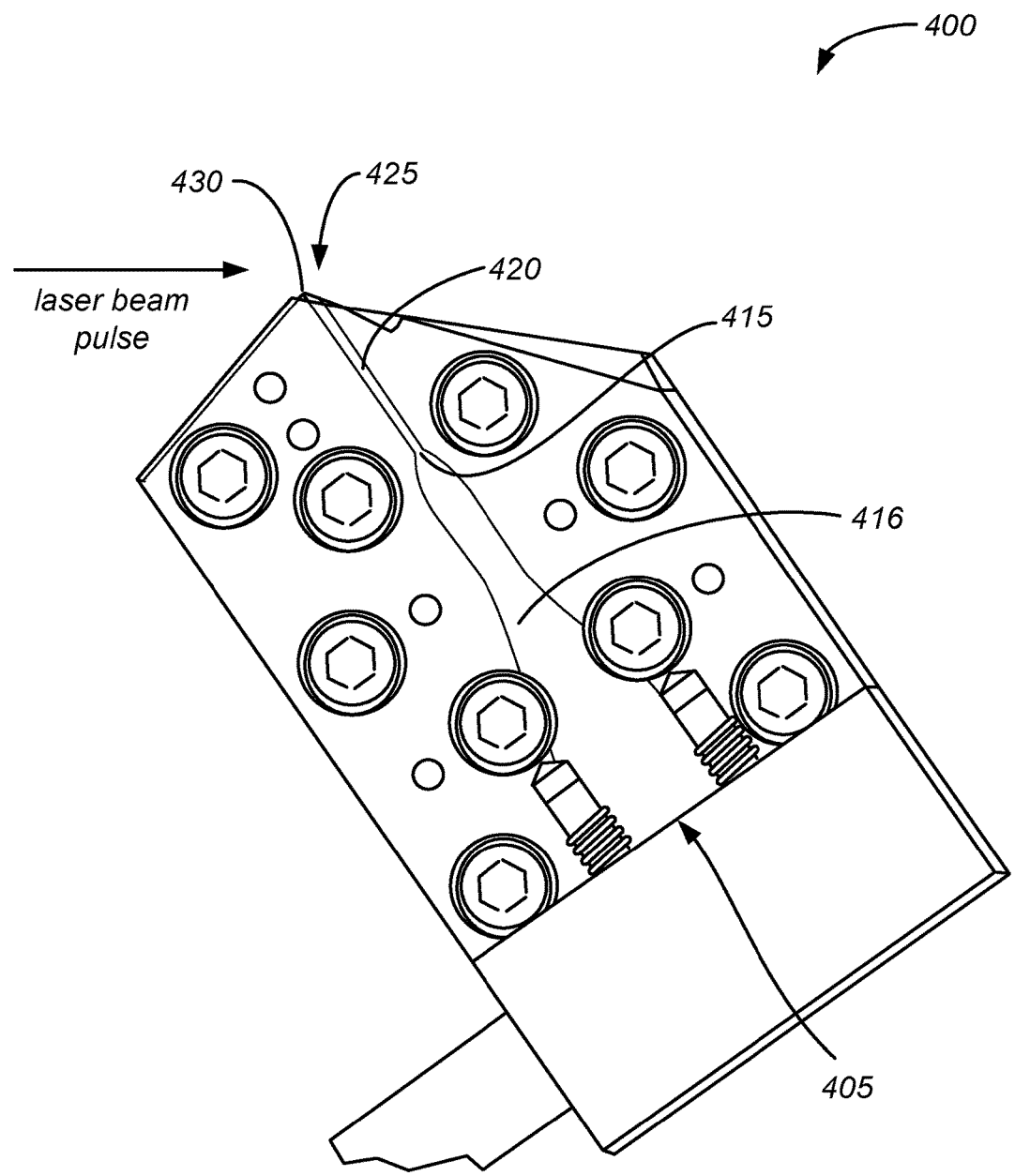
FIG. 4 shows an example of an illustration of a shock injector.

FIG. 4 shows an example of an illustration of a shock injector. In some embodiments, a shock injector 400 shown in FIG. 4 is similar to the shock injector 100 shown in FIGS. 1A and 1B. For example, in some embodiments, the shock injector 400 is configured to generate a gas flow similar to the gas flow that can be generated with the shock injector 100.

The shock injector 400 defines a gas inlet 405, a chamber 410, a throat 415, a channel 420, and a gas outlet 425. The gas inlet 405 is in fluid communication with the chamber 410. The chamber 410 is in fluid communication with the throat 415. The throat 415 is in fluid communication with the channel 420. The channel 420 is in fluid communication with the gas outlet 425. A gas input at the gas inlet 405 of the shock injector 400 will flow through the chamber 410, the throat 415, the channel 420, and exit the shock injector 400 through the gas outlet 425. Proximate the gas outlet 425, the channel 420 includes a ramp 430. The ramp 430 is inclined at an angle with respect to a direction of a flow of the gas at the gas outlet 425.

Figure 5A:
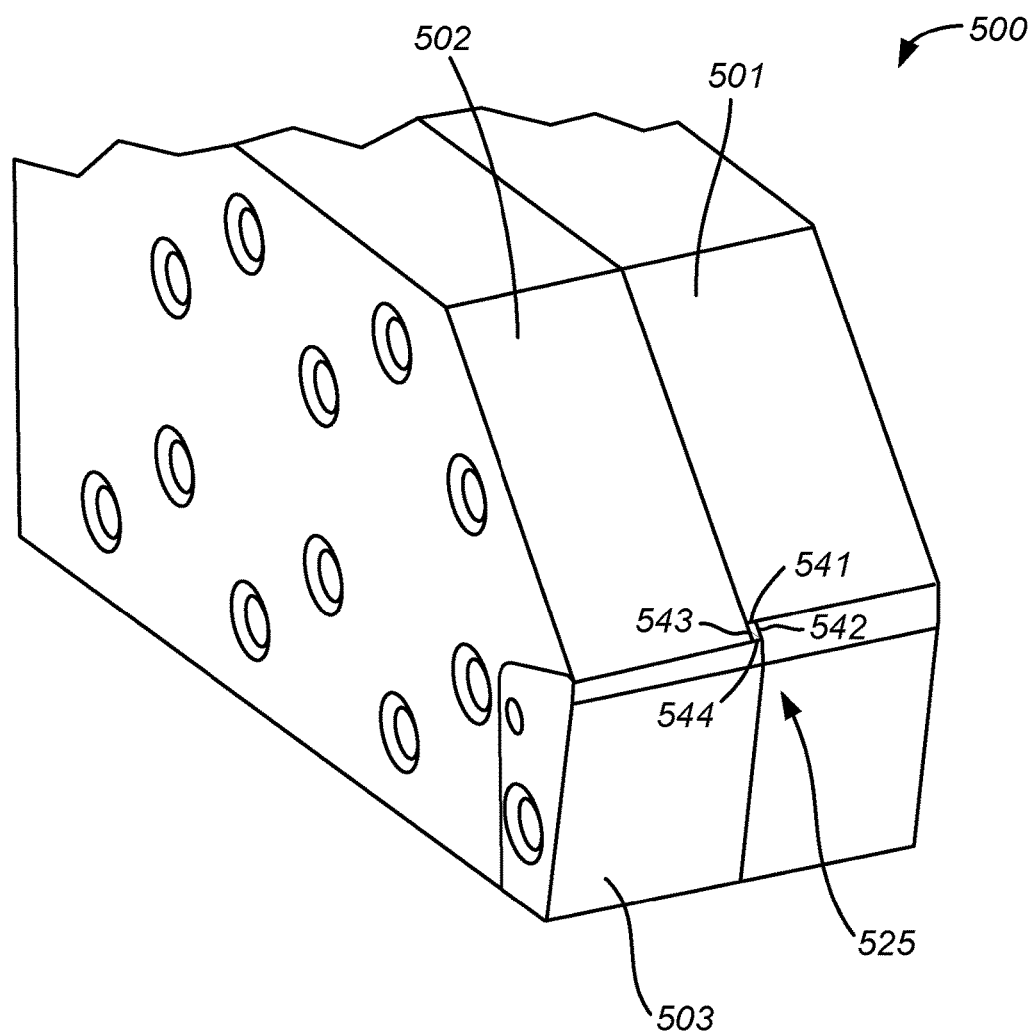
FIGS. 5A-5C show examples of illustrations of a shock injector.
Figure 5B:
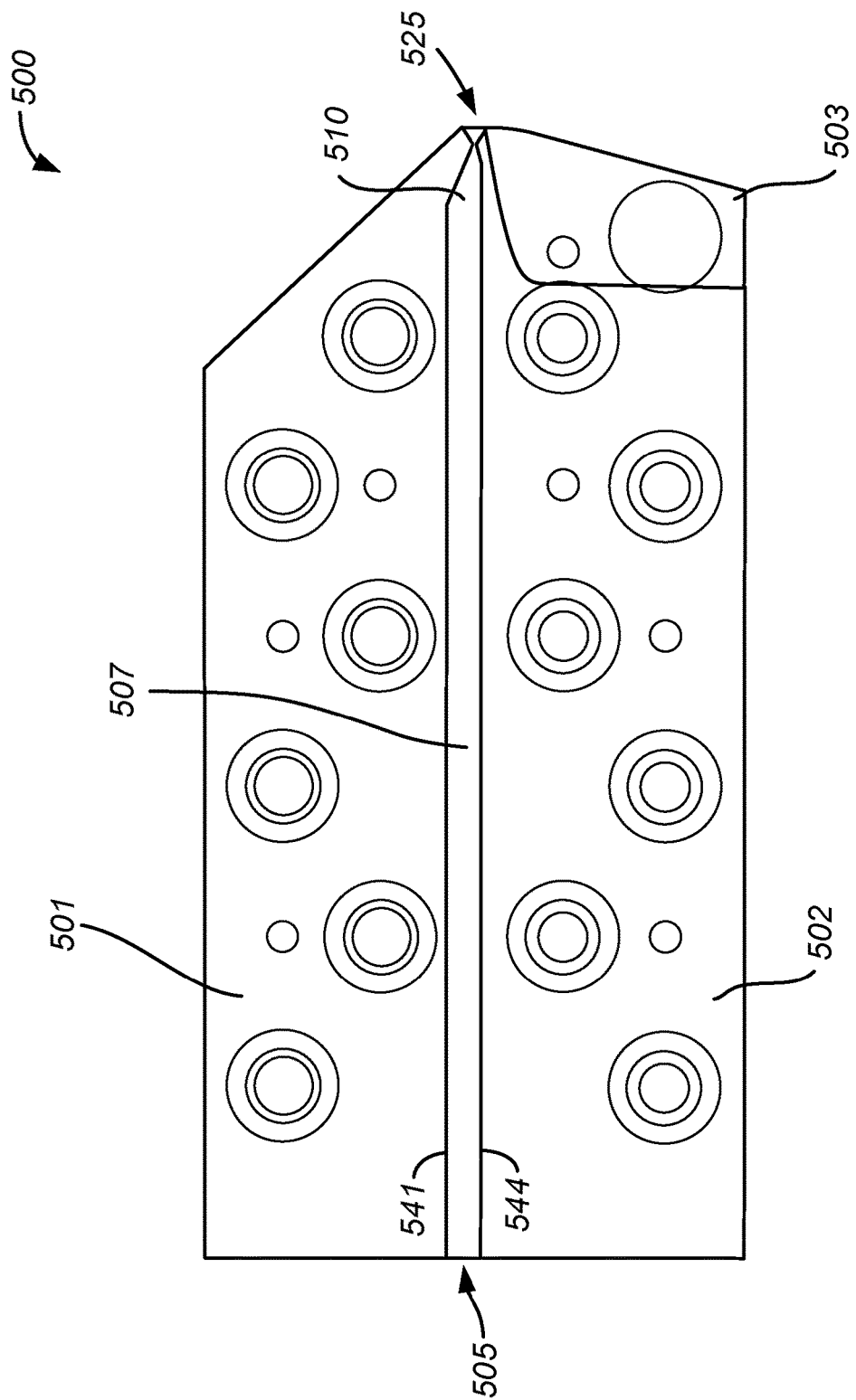
Figure 5C:
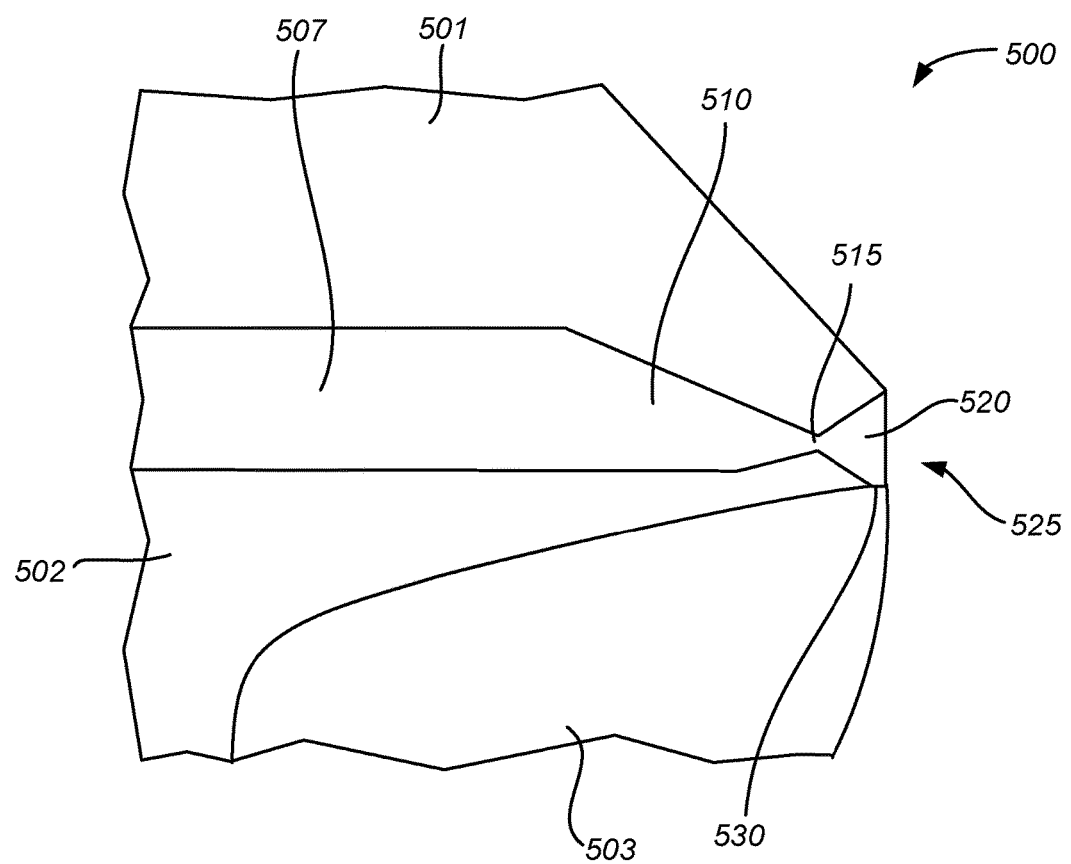

FIGS. 5A-5C show examples of illustrations of a shock injector. FIG. 5A shows an illustration of the end of a shock injector including the gas outlet. FIG. 5B shows an illustration of the gas flow pathway in a shock injector. FIG. 5C shows an enlarged illustration of the chamber, the throat, the channel, and the gas outlet of a shock injector. In some embodiments, a shock injector 500 shown in FIGS. 5A-5C is similar to the shock injector 100 shown in FIGS. 1A and 1B. For example, in some embodiments, the shock injector 500 is configured to generate a gas flow similar to the gas flow that can be generated with the shock injector 100.

The shock injector 500 defines a gas inlet 505, a channel 507, a chamber 510, a throat 515, a channel 520, and a gas outlet 525. The gas inlet 505 is in fluid communication with the channel 507. The channel 507 is in fluid communication with the chamber 510. The chamber 510 is in fluid communication with the throat 515. The throat 515 is in fluid communication with the channel 520. The channel 520 is in fluid communication with the gas outlet 525. A gas input at the gas inlet 505 of the shock injector 500 will flow through the channel 507, the chamber 510, the throat 515, the channel 520, and exit the shock injector 500 through the gas outlet 525.

In some embodiments, the shock injector 500 includes three blocks of material 501, 502, and 503. In some embodiments, the blocks of material 501, 502, and 503 comprise a polymer, such as an acrylic glass. In some embodiments, surfaces 541 and 542 of the block of material 501 and surface 543 and 544 of the block of material 502 define surfaces of the gas inlet 505, the channel 507, the chamber 510, the throat 515, the channel 520, and the gas outlet 525. In some embodiments, the surfaces 542 and 543 are substantially flat and substantially parallel to one another. In some embodiments, a distance the surfaces 542 and 543 is about 300 microns to 1 mm, or about 500 microns. In some embodiments, a distance between the surfaces 541 and 544 define dimensions of the gas inlet 505, the channel 507, the chamber 510, the throat 515, the channel 520, and the gas outlet 525 so that these features are distinguished from one another in the shock injector 500.

In some embodiments, a distance between the surfaces 541 and 544 defining the gas inlet 505 may be about 750 microns to 10 mm. In some embodiments, a distance between the surfaces 541 and 544 defining the gas outlet 525 may be about 250 microns to 1 mm.

In some embodiments, a distance between the surfaces 541 and 544 defining the throat 515 may be about 20 microns to 100 microns. In some embodiments, the throat 515 is configured to generate a supersonic flow of a gas when gas flows through the throat. The pressure of the gas and the dimension of the throat may be specified so that the gas has a supersonic velocity after passing through the throat 515. In some embodiments, the velocity of the gas after passing through the throat 515 is Mach 1.

In some embodiments, a distance between the surfaces 541 and 544 defining the channel 520 increases from the throat 515 to the gas outlet 525. In some embodiments, dimensions of the channel 520 are specified so that flow of a gas through the channel 520 is divergent after the gas passes through the throat 515. In some embodiments, dimensions of the channel 520 are specified so that a gas has a specified velocity or a specified Mach number (e.g., about Mach 2 to Mach 6, or about Mach 3) at the gas outlet 525. The channel 520 includes a ramp 530 that is positioned proximate or at the gas outlet 525. The ramp 530 is inclined at an angle with respect to a direction of a flow of the gas proximate a surface of the channel 520 prior to the ramp 530 (i.e., the surface 544 of the channel 520 that transitions to the ramp 530) at the gas outlet 525. The direction of the flow of the gas proximate the surface 544 of the channel 520 at the gas outlet 525 may generally be considered to be parallel to the surface 544 of the channel 520 before the ramp 530. In some embodiments, flow of the gas within about 5 microns of the surface 544 of the channel 520 is parallel to the surface 544.

In some embodiments, the ramp 530 is angled at about 15 degrees to 45 degrees, or about 30 degrees, with respect to the direction of the flow of the gas at the gas outlet, with the ramp 530 being angled towards the gas. In some embodiments, the ramp 530 is configured to generate an oblique shock wave in the gas when a gas is flowing through the shock injector 500.

In some embodiments, the ramp 530 is defined by the block of material 503. Defining the ramp 530 by the block of material 503 may allow for a sharp transition from the wall defining the channel 520 to the ramp 530. For example, using the block of material 503 may aid in avoiding smearing of the transition between the channel 520 and the ramp 530 with a tooling radius during fabrication. This may aid in the generation of an oblique shock wave when a gas is flowing through the shock injector 500.

The shock injectors 100 (FIGS. 1A and 1B), 400 (FIG. 4), and 500 (FIGS. 5A-5C) described above were fabricated using a polymer. In some embodiments, a shock injector is fabricated using a semiconductor or a metal. MEMS fabrication techniques and precision machining techniques can be used to fabricate a shock injector.

Figure 6:
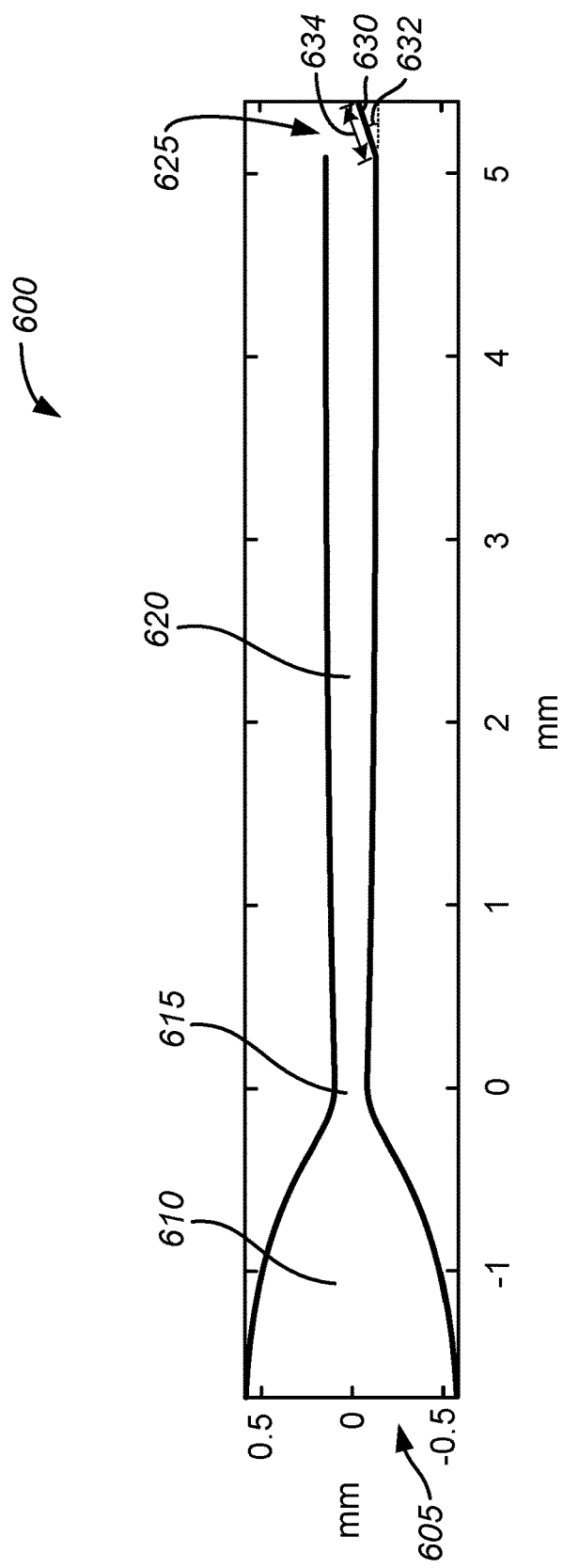
FIG. 6 shows an example of an illustration of a gas flow pathway defined by a shock injector.

FIG. 6 shows an example of an illustration of a gas flow pathway defined by a shock injector. The gas flow pathway 600 shown in FIG. 6 includes a gas inlet 605, a chamber 610, a throat 615, a channel 620, and a gas outlet 630. The channel 620 includes a ramp 630 that is positioned proximate the gas outlet 625. The ramp 630 is inclined at an angle 632 with respect to a direction of a flow of the gas at the gas outlet 625. In some embodiments, the ramp 630 is angled at about 15 degrees to 45 degrees, or about 30 degrees, with respect to the direction of the flow of the gas at the gas outlet, with the ramp 630 being angled towards the gas. In some embodiments, a length 634 of the ramp 630 is about 100 microns to 500 microns.

In some embodiments, the contours of the channel 620 are determined by the method of characteristics. The method of characteristics traces Mach waves through the channel. Doing this, it can be determined where a Mach wave will reflect at a wall of the channel. The contour of the walls of the channel can be changed at points where the Mach waves will reflect so that the Mach waves are cancelled out at the walls of the channel 620. In some embodiments, the contours of the channel 620 are specified so that no shock waves are generated in the gas flow until the gas flows past the ramp 630.

One goal of using a shock injector in a LPA is to generate stable electrons using a low laser energy (e.g., a laser energy on the order of 10 mJ). A shock injector can also be used in LPAs with higher laser energies. Advantages of a shock injector, compared to other target generation devices, include simplified fabrication techniques and better scalability to smaller gas jets, such as those that would be used for a fiber optic-based electron therapy device, for example.

A shock injector as described herein can be used in many fields. For example, a shock injector may be used in a LPA that is part of a medical device for electron beam therapy. Medical devices for electron beam therapy are described in U.S. Pat. No. 8,878,464 (Laser accelerator driven particle brachytherapy devices, systems, and methods), which is herein incorporated by reference.

A shock injector may also be used in research as a high repetition-rate LPA target device for an electron source for ultrafast electron diffraction (UED). Coupled with the developing fiber optic technology, a compact UED imaging device that provides high spatial and temporal resolution could be developed for use in manufacturing, biology, and chemistry. A shock injector may also be used for a compact Bremsstrahlung source for security applications.

Figure 7A:
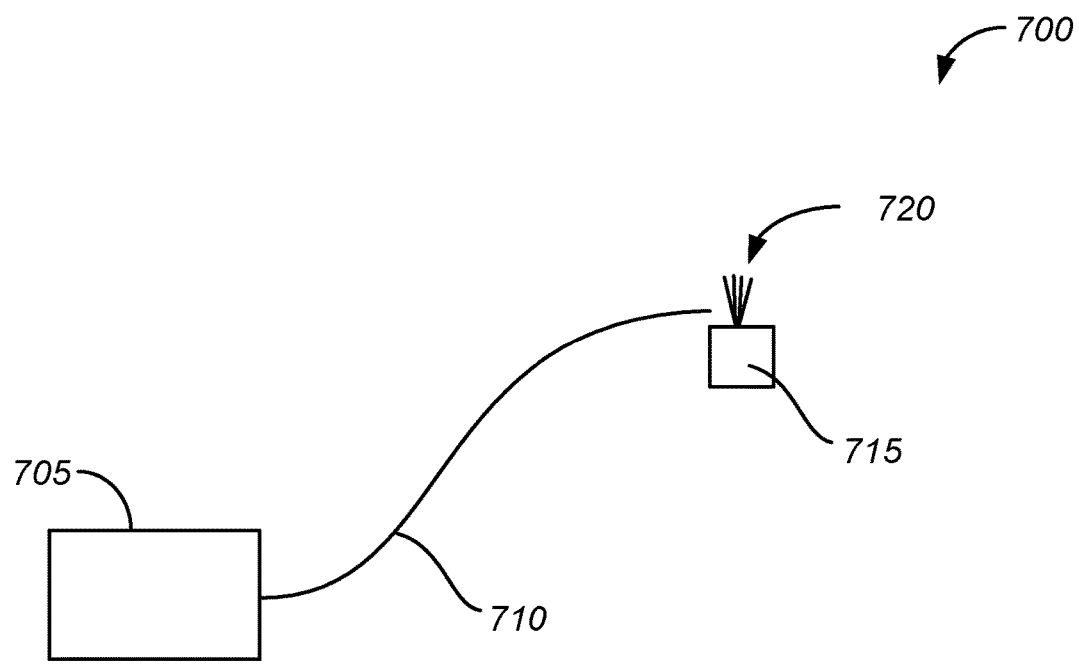
FIG. 7A shows an example of an illustration of a LPA incorporating a shock injector.

FIG. 7A shows an example of an illustration of a LPA incorporating a shock injector. The LPA 700 shown in FIG. 7A includes a laser system 705, an optical fiber 710, and a shock injector 715. The laser system 705 is coupled to the optical fiber 710. The laser system 705 can be any number of different laser systems. For example, the laser system 705 may be a titanium-sapphire laser. Titanium-sapphire lasers are tunable lasers that can emit red and near-infrared light in the range from 650 nanometers (nm) to 1100 nm. In some embodiments, the laser system 705 emits light at about 800 nm. In some embodiments, the laser system 705 is operable to generate about 10 mJ laser energy and about 10 femtosecond laser pulses. With adjustments to the densities of the gas in the gas flow from the shock injector 715, almost any laser wavelength can be used with the shock injector 715.

The optical fiber 710 is configured to transport laser pulses generated by the laser system 705 to a gas stream 720 emitted by the shock injector 715. An end of the optical fiber 710 is positioned to direct a laser pulse through a gas when gas is flowing from the gas outlet of the shock injector 715. The laser pulse is directed through the gas flow close to the gas outlet of the shock injector so that the two density regions in the gas flow are well defined. Further, the closer the laser pulse is to the gas outlet of the shock injector, the greater the gas density in the first region of the gas flow and the greater the gas density in the second region of the gas flow. For example, in some embodiments, the laser pulse impinges the gas flow about 150 microns to 1 mm, or about 300 microns, after the gas flow exits the shock injector 715. In some embodiments, the laser pulse impinges the gas flow about 150 microns to 1 mm, or about 300 microns, from the gas outlet of the shock injector 715.

In some embodiments, the optical fiber 710 comprises a hollow optical fiber. In some embodiments, the optical fiber 710 comprises a hypocycloid photonic crystal fiber. Hypocycloid photonic crystal fibers are available, for example, from GLOphotonics (Limoges, France). In some embodiments, a diameter of the optical fiber is about 200 microns to 1200 microns, or about 300 microns. In some embodiments, a length of the optical fiber is about 1 meter to 5 meters, or about 3 meters. The optical fiber may also increase the bandwidth of the laser pulse, which allows for compression of the laser pulse. For example, the laser pulse may be compressed from about 40 femtoseconds (fs) to about 12 fs.

In some embodiments, when the LPA 700 is in operation and the optical fiber 710 is a hollow optical fiber, there is a gas (e.g., air) in the hollow optical fiber. In some embodiments, when the LPA 700 is in operation and the optical fiber 710 is a hollow optical fiber, the hollow part of the hollow optical fiber is under vacuum; i.e., gasses are removed from the hollow part of the hollow optical fiber. In some embodiments, the energy of the laser pulse is determined, in part, by the energy of a laser pulse that damages the optical fiber; the energy of the laser pulse may be less than the energy of a laser pulse that damages the optical fiber. In some embodiments, the optical fiber 710 transmits up to about 100 mJ or up to about 10 mJ of laser energy without being damaged.

In some embodiments, the shock injector 715 is a shock injector similar to a shock injector described above, such as the shock injector 100 (FIGS. 1A and 1B), the shock injector 400 (FIG. 4), or the shock injector 500 (FIGS. 5A-5C).

Figure 7B:
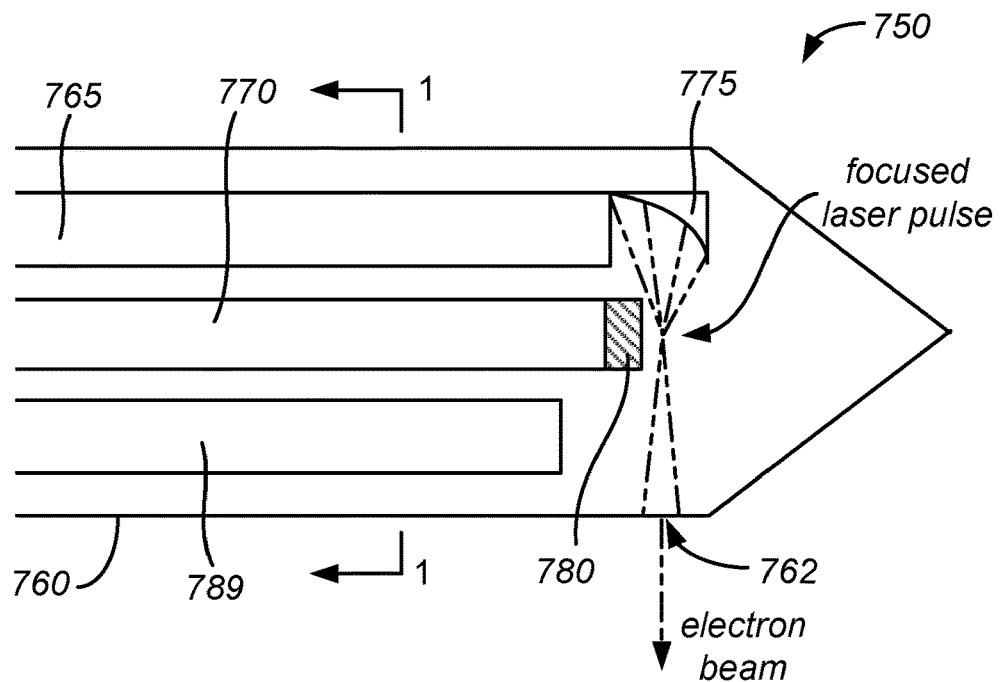
FIGS. 7B and 7C show examples of illustrations of a device for use in medical procedures.
Figure 7C:
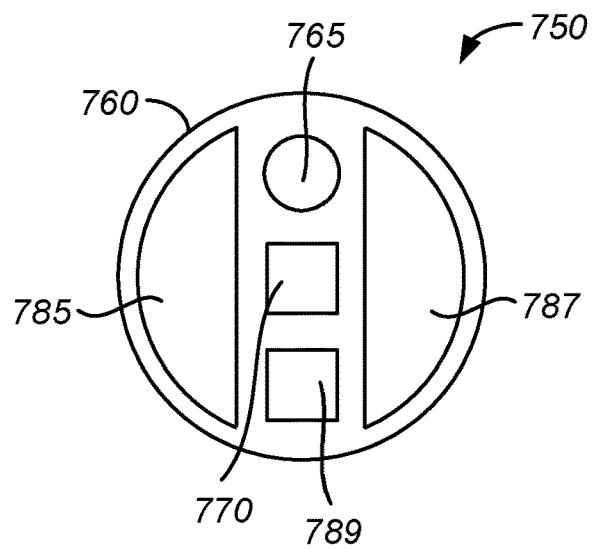

FIGS. 7B and 7C show examples of illustrations of a device for use in medical procedures. For example, the device could be used in brachytherapy. Brachytherapy is a type of radiation therapy that can be used to treat cancer in which a radiation source is placed inside or next to the area requiring treatment. A catheter can be used to contain the radiation source. A catheter is a medical device that can be inserted in the body to treat diseases or perform to surgical procedures. FIG. 7B shows a cross-sectional illustration along a length of a catheter. FIG. 7C shows a cross-sectional illustration along a diameter of a catheter. FIG. 7C shows an illustration through line 1-1 in FIG. 7B.

As shown in FIGS. 7B and 7C, a device 750 includes a catheter 760. In some embodiments, the catheter is about 1 mm to 2 mm in diameter, or about 1.5 mm in diameter. Disposed within the catheter 760 are an optical fiber 765 and a gas delivery tube 770. In some embodiments, the optical fiber 765 and the gas delivery tube 770 are substantially parallel to one another. In some embodiments, a diameter of the optical fiber 765 is about 200 microns to 1200 microns, or about 300 microns. In some embodiments, an outside diameter (e.g., if the tube has a circular cross-section) or dimension (e.g., if the tube has a square or rectangular cross-section) of the gas delivery tube 775 is about 175 microns to 525 microns, or about 350 microns.

Coupled to the end of the gas delivery tube 770 is a shock injector 780. In some embodiments, the shock injector 780 defines a gas inlet, a chamber, a throat, a channel including a ramp, and a gas outlet. The shock injector 780 may define any a gas flow path similar to any of the shock injectors described above. A block of material defining the gas flow path of the shock injector 780 may be smaller, however, than the shock injectors described above so that the shock injector 780 can be disposed within the catheter 760.

Positioned proximate or near an end of the optical fiber 765 is a focusing element 775. In some embodiments, the focusing element 775 comprises a reflective surface that focuses a laser pulse from the optical fiber 765 on to a gas flow from the shock injector 780. In some embodiments, the focusing element 775 focuses a laser pulse and changes the direction of the laser pulse by about 90° so that the laser pulse impinges on a gas flow from the shock injector 780. In some embodiments, the focusing element 775 comprises a concave mirror, also referred to as a converging mirror. A concave mirror has a reflecting surface that bulges inward (i.e., away from the incident light). Concave mirrors reflect light inward to one focal point.

In some embodiments, the catheter 760 comprises a polymer, such as silicone rubber, nitinol, nylon, polyurethane, polyethylene terephthalate (PET), latex, or a thermoplastic elastomer, for example. In some embodiments, the material of the catheter 760 allows for electrons to pass through the material without significant energy loss. For example, accelerated electrons generated in a laser pulse impinging on a gas flow in the catheter 760 can travel though the catheter 760 at position 762 in the catheter 760.

In some embodiments, the catheter 760 also houses further components. Such components may include exhaust channels 785 and 787 for gas that flows through the shock injector 780. A channel 789 may house a cooling devices (e.g., a cooling loop) and characterization devices to characterize the operation of catheter 760. For example, such characterization devices may include devices to measure the gas flow rate, characteristics of the laser pulse, and characteristics of accelerated electrons. Further channels, such as additional exhaust channels and additional channels for cooling devices and characterization devices, may be housed in the catheter 760, space permitting.

Figure 8:
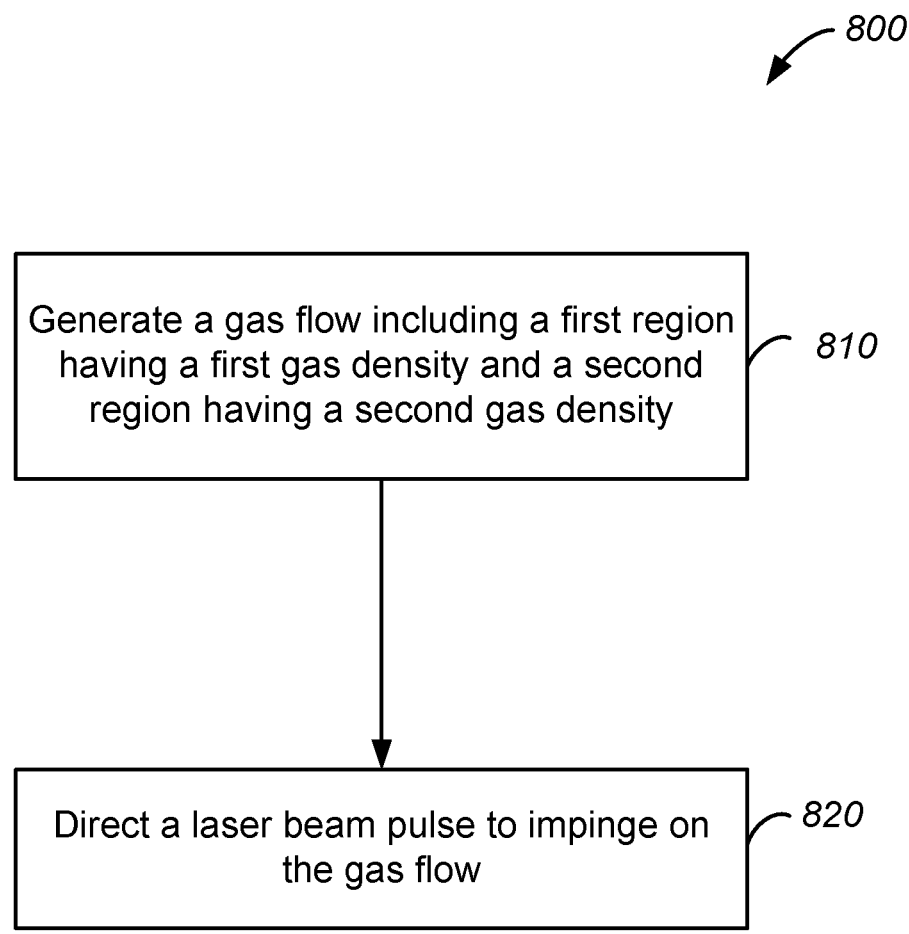
FIG. 8 shows an example of a flow diagram illustrating a method of generating a pulse of accelerated electrons.

FIG. 8 shows an example of a flow diagram illustrating a method of generating a pulse of accelerated electrons. The method 800 shown in FIG. 8 could be performed with the LPA 700 shown in FIG. 7A. At block 810 of the method 800, a gas flow including a first region having a first gas density and a second region having a second gas density is generated.

In some embodiments, the first gas density is about 1.5 to 2.5 times, or about 2 times, the second gas density. In some embodiments, the first gas density is about $1.3 \times 10^{18}$ atoms per centimeter cubed (atoms/cm$^3$) to $6.3 \times 10^{18}$ atoms/cm$^3$, and the second gas density is about $6.5 \times 10^{17}$ atoms/cm$^3$ to $3.1 \times 10^{18}$ atoms/cm$^3$. The transition between the first gas region and the second gas region is an oblique shock wave. In some embodiments, a width of the transition between the first gas region and the second gas region is less than about 5 microns. In some embodiments, the gas used to generate the gas flow is selected from a group consisting of hydrogen, helium, neon, argon, krypton, and xenon.

In some embodiments, a shock injector is provided before block 810. In some embodiments, the shock injector is a shock injector described above, such as the shock injector 100 (FIGS. 1A and 1B), the shock injector 400 (FIG. 4), or the shock injector 500 (FIGS. 5A-5C). In some embodiments, a gas pressure at the gas inlet of the shock injector is about 1 pound per square inch absolute (psia) to 100 psia. Pounds per square inch absolute indicates that the pressure is relative to a vacuum rather than the ambient atmospheric pressure. In some embodiments, a rate of gas flow at the gas inlet and at the gas outlet of the shock injector is about 0.5 liters per minute (L/min) to 2 L/min at standard temperature and pressure (stp). In some embodiments, a velocity of the gas after passing through the throat of the shock injector is Mach 1. In some embodiments, a velocity of the gas at the gas outlet of the shock injector is about Mach 2 to Mach 6, or about Mach 3.

At block 820, a laser pulse is directed to impinge on the gas flow. The laser pulse travels through the first region of the gas flow and then the second region of the gas flow. The laser pulse generates a pulse of accelerated electrons. In some embodiments, the laser pulse has an energy of less than about 100 mJ, or less than about 10 mJ. In some embodiments, the laser pulse has a duration of about 10 femtoseconds (fs) to 40 fs, or about 12 fs. In some embodiments, a plurality of laser pulses can be delivered to the gas flow at a rate of about 1 kHz to 1 MHz or about 1 kHz to 100 kHz. In some embodiments, the laser pulse has a wavelength of about 600 nm to 2000 nm, or about 800 nm.

In some embodiments, a width of the first region of the gas flow that the laser pulse travels through is about 100 microns to 300 microns, or about 200 microns. In some embodiments, a width of the second region of the gas flow that the laser pulse travels through is about 75 microns to 225 microns, or about 150 microns. In some embodiments, the laser pulse creates a plasma having a density of about $1 \times 10^{19}$ electrons per centimeter cubed (electrons/cm$^3$) to $5 \times 10^{19}$ electrons/cm$^3$ in the first region. In some embodiments, the laser pulse creates a plasma having a density of about $5 \times 10^{18}$ electrons/cm$^3$ to $2.5 \times 10^{19}$ electrons/cm$^3$ in the second region.

In some embodiments, electrons in the pulse of accelerated electrons have energies of about 1 MeV to 10 MeV. In some embodiments, the pulse of accelerated electrons has a duration of about 10 fs to 40 fs, or about 12 fs.

Figure 9:
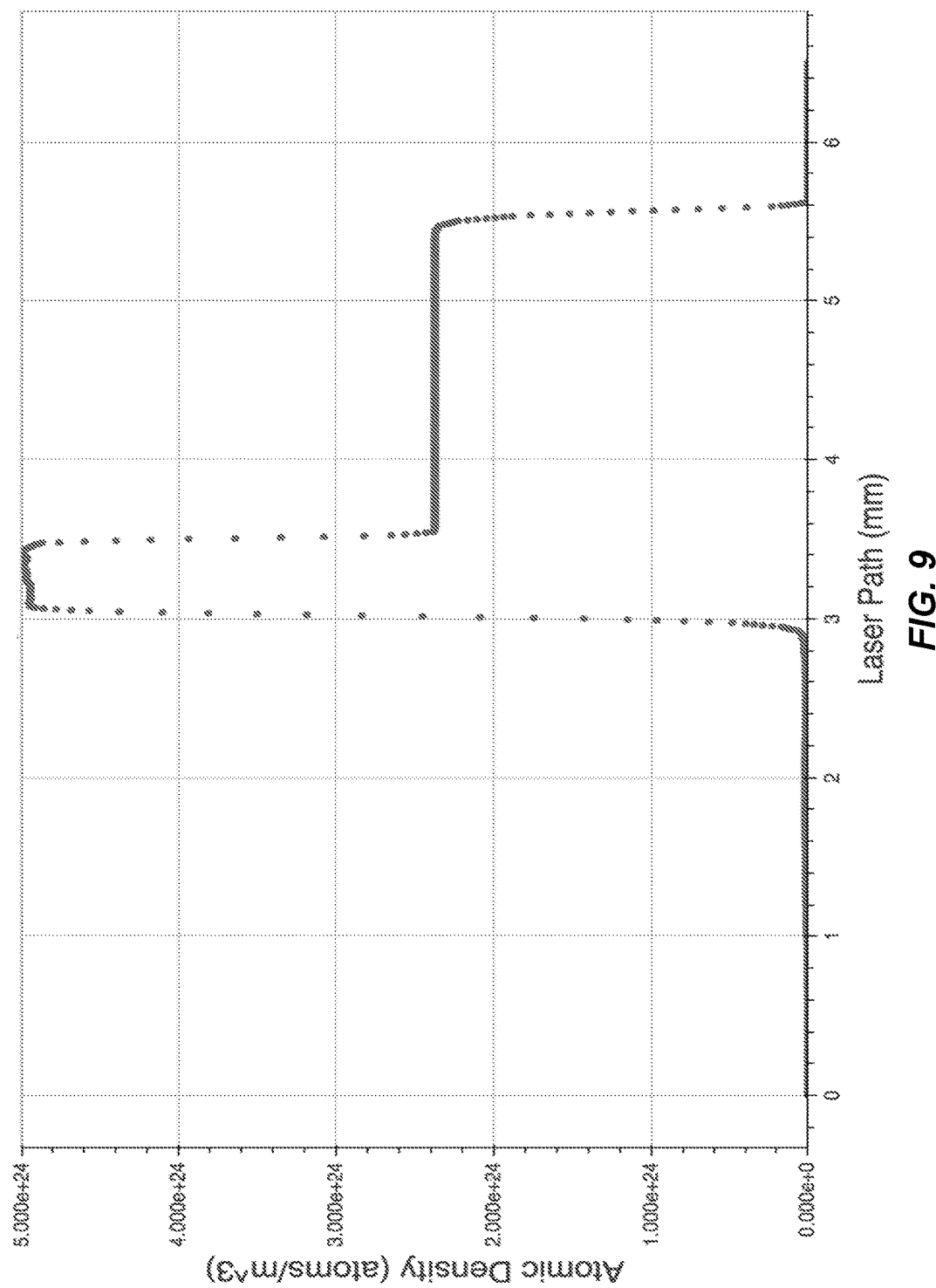
FIG. 9 shows an example of the results of a compressible flow simulation of a shock injector.

FIG. 9 shows an example of the results of a compressible flow simulation of a shock injector. In this simulation, the throat and the channel of the shock injector were contoured to deliver a parallel, Mach 3 flow at the gas outlet. The ramp at the end of the channel near the gas outlet created an oblique shock creating two separate density regions. Because the thickness of the shock is a particle effect, compressible fluid simulations are not capable of predicting the thickness of the density transition. Direct Simulation Monte Carlo (DSMC) was used to determine the thickness of the shock.

Figure 10:
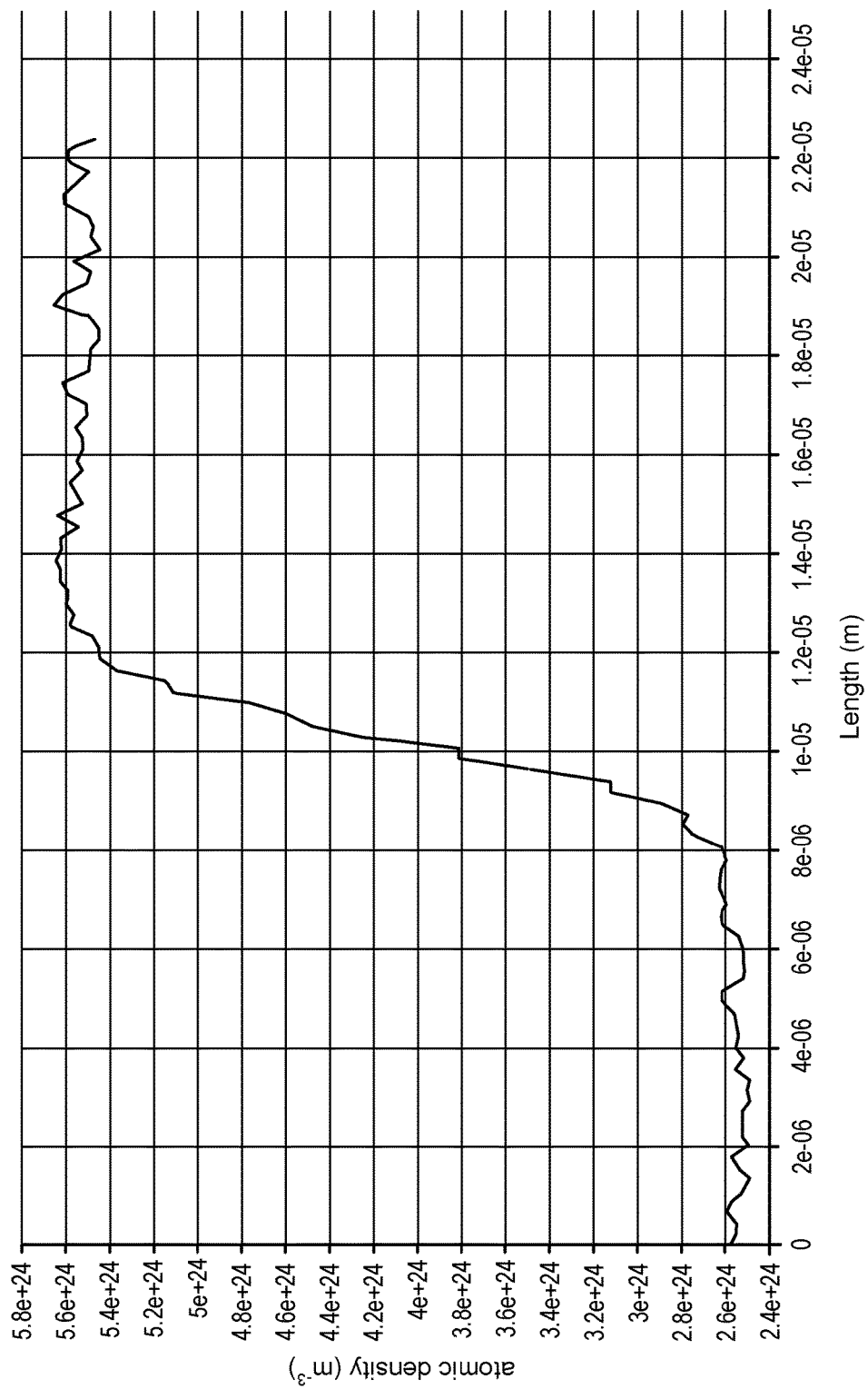
FIG. 10 shows an example of the results of a Direct Simulation Monte Carlo (DSMC) simulation of a shock injector.

FIG. 10 shows an example of the results of a DSMC simulation of a shock injector. DSMC simulations were performed to confirm that a shock injector can generate a density transition between two gas regions over a distance of about 5 microns (e.g., the plasma wavelength) or less. DSMC simulations are capable of resolving length scales on the order of the mean free path (or the average interparticle spacing) of gas atoms. DSMC uses macro-particles in a probabilistic simulation to capture events that occur on the length scale of the intermolecular spacing.

In the DSMC simulations, Mach 3 flow was initialized at the exit (simulation boundary). The ramp of the supersonic nozzle created an oblique shock and generated two separate gas density regions. The results of the simulations verified that the density transition in a gas from one design of a shock injector occurs over about 3 microns, which is below the plasma wavelength. In these results, the length of the density transition was defined as the density difference divided by the maximum density gradient.

FIG. 11 shows an example of the results of a laser plasma particle in a cell simulation. In FIG. 11, $a_0$ is a normalized quantity for laser intensity. These simulations show that the generation of a 10 MeV electron beam is possible using a 10 mJ, 12 fs laser pulse and a sharp density change in a gas. Such a sharp density change in a gas can be generated by any of the shock injectors described herein.

In the foregoing specification, the invention has been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

What is claimed is:

1. A device comprising:
a block of material, the block of material defining:
 a gas inlet;
 a chamber in fluid communication with the gas inlet;
 a throat in fluid communication with the chamber, the throat being configured to generate a supersonic flow of a gas when the gas flows through the throat;
 a channel in fluid communication with the throat; and
 a gas outlet in fluid communication with the channel, the channel including a ramp that is positioned proximate the gas outlet, the ramp being inclined at an angle with respect to a direction of a flow of the gas proximate a surface of the channel prior to the ramp at the gas outlet;
 the chamber, the throat, and the channel being defined by a first, a second, a third, and a fourth surface, the first surface and the second surface being substantially flat surfaces and being substantially parallel to one another, and a distance between a third surface and a fourth surface defining the channel increasing from a region of the channel proximate the throat to a region proximate the gas outlet.

2. The device of claim 1, wherein the ramp is angled at about 15 degrees to 45 degrees with respect to the direction of the flow of the gas at the gas outlet, and wherein the ramp is angled towards the gas.

3. The device of claim 1, wherein a distance between the first surface and the second surface is about 300 microns to 1 millimeter.

4. The device of claim 1, wherein a distance between the third surface and the fourth surface defining the throat is about 20 microns to 100 microns.

5. The device of claim 1, wherein a distance between the third surface and the fourth surface defining the gas outlet is about 250 microns to 1 millimeter.

6. The device of claim 1, wherein the block of material comprises an acrylic glass.

7. The device of claim 1, wherein the ramp is configured to generate an oblique shock wave in a flow of the gas when the gas is flowing through the device.

8. The device of claim 1, wherein the channel is configured not to generate any shock waves in the gas until the gas flows past the ramp.

9. The device of claim 1, wherein the device is configured to generate a flow of a gas including a first region having a first gas density and a second region having a second gas density, and wherein the first gas density is about 1.5 to 2.5 times the second gas density.

10. The device of claim 1, wherein the gas has a velocity of about Mach 2 to Mach 6 at the gas outlet.

11. An apparatus comprising:
a device comprising:
 a block of material, the block of material defining:
  a gas inlet,
  a chamber in fluid communication with the gas inlet,
  a throat in fluid communication with the chamber, the throat being configured to generate a supersonic flow of a gas when the gas flows through the throat,
  a channel in fluid communication with the throat, and
  a gas outlet in fluid communication with the channel, the channel including a ramp that is positioned proximate the gas outlet, the ramp being inclined at an angle with respect to a direction of a flow of the gas proximate a surface of the channel prior to the ramp at the gas outlet,
  the chamber, the throat, and the channel being defined by a first, a second, a third, and a fourth surface, the first surface and the second surface being substantially flat surfaces and being substantially parallel to one another, and a distance between a third surface and a fourth surface defining the channel increasing from a region of the channel proximate the throat to a region proximate the gas outlet;
a laser system configured to generate a laser pulse; and
an optical fiber, the optical fiber being coupled to the laser system and configured to guide the laser pulse, an end of the optical fiber positioned to direct the laser pulse through the gas when the gas is flowing from the gas outlet.

12. The apparatus of claim 11, wherein the laser system comprises a titanium-sapphire laser.

13. The apparatus of claim 11, wherein the optical fiber comprises a hypocycloid photonic crystal fiber.

14. A method comprising:
providing a device, the device including:
 a block of material, the block of material defining:
  a gas inlet,
  a chamber in fluid communication with the gas inlet,
  a throat in fluid communication with the chamber, the throat being configured to generate a supersonic flow of a gas when the gas flows through the throat,
  a channel in fluid communication with the throat, and
  a gas outlet in fluid communication with the channel, the channel including a ramp that is positioned proximate the gas outlet, and the ramp being inclined at an angle with respect to a direction of the flow of the gas proximate a surface of the channel prior to the ramp at the gas outlet, the chamber, the throat, and the channel being defined by a first, a second, a third, and a fourth surface, the first surface and the second surface being substantially flat surfaces and being substantially parallel to one another, a distance between a third surface and a fourth surface defining the channel increasing from a region of the channel proximate the throat to a region proximate the gas outlet;

generating a flow of the gas using the device, the flow of the gas including a first region having a first gas density and a second region having a second gas density, a transition region between the first region and the second region being an oblique shock wave and having a width of less than about 5 microns, the first gas density being about 1.5 to 2.5 times the second gas density; and directing a laser pulse to impinge on the gas flow, the laser pulse travelling through the first region and then the second region, the laser pulse generating a pulse of accelerated electrons.

15. The method of claim 14, wherein the gas is selected from a group consisting of hydrogen, helium, neon, argon, krypton, and xenon.

16. The method of claim 14, wherein a rate of flow of the gas through the device is about 0.5 liter per minute to about 2 liters per minute.

17. The method of claim 14, wherein the laser pulse has an energy of less than about 100 millijoules, and wherein the laser pulse has a duration of about 12 femtoseconds to 40 femtoseconds.

18. The method of claim 14, wherein electrons in the pulse of accelerated electrons have energies of about 1 MeV to 10 MeV.

19. The method of claim 14, wherein the pulse of accelerated electrons has a duration of about 12 femtoseconds to 40 femtoseconds.

* * * * *